United States Patent
Han et al.

(10) Patent No.: US 7,371,530 B2
(45) Date of Patent: May 13, 2008

(54) MICRO PCR DEVICE, METHOD FOR AMPLIFYING NUCLEIC ACIDS USING THE MICRO PCR DEVICE, AND METHOD FOR MEASURING CONCENTRATION OF PCR PRODUCTS USING THE MICRO PCR DEVICE

(75) Inventors: Jung-im Han, Seoul (KR); Kwang-wook Oh, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 119 days.

(21) Appl. No.: 11/066,910

(22) Filed: Feb. 25, 2005

(65) Prior Publication Data
US 2005/0191686 A1    Sep. 1, 2005

(30) Foreign Application Priority Data
Feb. 28, 2004    (KR) .................. 10-2004-0013779

(51) Int. Cl.
*C12Q 1/68*     (2006.01)
*C12P 19/34*    (2006.01)

(52) U.S. Cl. .................. 435/6; 435/91.1; 435/91.2

(58) Field of Classification Search .................. None
See application file for complete search history.

(56) References Cited

U.S. PATENT DOCUMENTS

| | | | |
|---|---|---|---|
| 2002/0072054 A1* | 6/2002 | Miles et al. .................. | 435/6 |
| 2003/0143604 A1* | 7/2003 | Storhoff et al. .................. | 435/6 |
| 2005/0123937 A1* | 6/2005 | Thorp et al. .................. | 435/6 |
| 2005/0191651 A1* | 9/2005 | Franzen et al. .................. | 435/6 |

* cited by examiner

*Primary Examiner*—Young J. Kim
(74) *Attorney, Agent, or Firm*—Cantor Colburn LLP

(57) ABSTRACT

Provided is a micro PCR device. The micro PCR device includes a PCR chamber having electrodes. First primers of PCR primer sets are immobilized on the surfaces of the electrodes and second primers labeled with nanoparticles of the PCR primer sets are added to the PCR chamber.

9 Claims, 12 Drawing Sheets

(a)

(b)

(c)

MICRO PCR DEVICE, METHOD FOR AMPLIFYING NUCLEIC ACIDS USING THE MICRO PCR DEVICE, AND METHOD FOR MEASURING CONCENTRATION OF PCR PRODUCTS USING THE MICRO PCR DEVICE

BACKGROUND OF THE INVENTION

This application claims priority from Korean Patent Application No. 10-2004-0013779, filed on Feb. 28, 2004, in the Korean Intellectual Property Office, the disclosure of which is incorporated herein in its entirety by reference.

1. Field of the Invention

The present invention relates to a micro polymerase chain reaction (PCR) device, a method for amplifying nucleic acids using the micro PCR device, and a method for measuring the concentration of PCR products using the micro PCR device.

2. Description of the Related Art

A traditional PCR provides the qualitative results of amplified DNAs by an electrophoresis at the end-point of PCR, but has many problems such as inaccuracy of the quantitative detection of DNAs. Therefore, a Real-Time PCR has been developed to allow for the quantitative assay of amplified DNAs by detecting the intensity of a fluorescent signal, which is in proportional to the concentration of the amplified DNAs, using an optical detection system.

A quantitative assay of DNAs is essential for studying disease treatments and DNA expression. For example, in order to ensure a successful medicinal therapy for patients infected with hepatitis B virus (HBV), the drug resistance to HBV must be tested by periodically detecting the concentration of HBV in a blood stream using a Real-Time PCR.

A conventional Real-Time PCR requires many optical devices such as a laser source, a micromirror, a microscope, and a filter, and an expensive fluorescent dye. In addition, because a conventional Real-Time PCR chip is based on the principle of detecting a fluorescent signal, there are many disadvantages in terms of miniaturization (chip formation) and economical efficiency.

In order to solve this problem, an effort was made to electrically detect DNAs using capillary electrophoresis (CE). This method allows for a qualitative assay, but has many problems for a quantitative assay. In addition, the transfer of PCR products to a CE detection system using a micro-channel after the completion of PCR is a laborious process and a high voltage is required. Therefore, requirements of economical efficiency and miniaturization are not satisfied.

U.S. patent application Publication No. 2002/0072054A1, filed by Miles et al., is based on the concept that as the concentration of DNAs increases during PCR, impedance decreases and conductivity increases. However, this application is concerned with a PCR chip for end-point detection and has no relevance to Real-Time PCR. In addition, there is a problem in that an ionically labeled probe must be used to detect amplified PCR products.

Meanwhile, according to conventional methods for detecting PCR products using an electrical or chemical signal as described above, measurement sensitivity and reproducibility are low, which makes it difficult to obtain reliable results. This is because components of a PCR mixture, such as proteins, ions, and stabilizers, are nonspecifically adsorbed to surfaces of electrodes detecting an electrical signal.

The present invention has been made in view of these problems. According to the present invention, one primer of a primer set is immobilized on surfaces of electrodes disposed in a PCR chamber, and the other primer labeled with nanoparticles is added to a PCR mixture. PCR is performed on the surfaces of the electrodes using the primer set and PCR products can be detected in real-time. Therefore, high detection sensitivity and reproducibility can be ensured. Furthermore, since various electrochemical detection methods can be used in detecting the PCR products, accuracy of the detection result can be increased.

Such performance enhancements of the present invention can be elucidated as follows. When self-assembled monolayers are formed by immobilizing primers on the surfaces of electrodes, nonspecific adsorption of other nucleic acids or proteins on the surfaces of the electrodes is almost completely prevented. Furthermore, since electrochemical detection is carried out for components immobilized on the surfaces of the electrodes, not the PCR mixture, detection sensitivity is enhanced. In addition, since the PCR products are immobilized on the surfaces of the electrodes, factors inhibiting the electrochemical detection can be removed by washing the electrodes, thereby enhancing reproducibility.

SUMMARY OF THE INVENTION

The present invention provides a micro PCR device that can detect PCR products in real-time with high sensitivity and reproducibility using nanoparticles without transferring the PCR products to a separate detection system.

The present invention also provides a method for amplifying nucleic acids using the micro PCR device.

The present invention also provides a method for measuring the concentration of PCR products using the micro PCR device.

According to an aspect of the present invention, there is provided a micro PCR device including a PCR chamber having electrodes, first primers of PCR primer sets being immobilized on the surfaces of the electrodes and second primers labeled with nanoparticles of the PCR primer sets being added to the PCR chamber.

The micro PCR device may further include a PCR product detection unit detecting in real-time PCR products produced on the surfaces of the electrodes using an electrochemical detection method. The electrochemical detection method may be a voltammetric detection method, a potentiometric detection method, an amperometric detection method, or an impedimetric detection method.

The micro PCR device may further include components commonly used in PCR devices, for example a heater, a cooler, and a temperature adjuster.

The PCR chamber may be made of a material that can withstand a thermal cycle during PCR, such as quartz, glass, and silicon. The material for the PCR chamber is well known to ordinary persons skilled in the art.

According to another aspect of the present invention, there is provided a method for amplifying nucleic acids, which includes: (a) immobilizing first primers of PCR primer sets on surfaces of electrodes disposed in a PCR chamber; (b) adding second primers labeled with nanoparticles of the PCR primer sets to the PCR chamber; and (c) performing PCR. The PCR may be performed on the surfaces of the electrodes.

Throughout the specification, the term "PCR mixture" refers to a reaction solution in which a thermal cycling reaction is carried out for nucleic acid amplification. The PCR mixture includes dNTPs, ions such as $Mg^{2+}$, oligonucleotides such as the second primers, and proteins such as polymerase.

The term "PCR" refers to a polymerase chain reaction that amplifies DNAs by repeated cycles of denaturation, annealing, and extension. The PCR is well known in ordinary persons skilled in the art. The temperature and duration of each of the denaturation, the annealing, and the extension can be appropriately adjusted considering a polymerase, a target nucleic acid sequence to be amplified, and a primer sequence.

According to yet another aspect of the present invention, there is provided a method for measuring the concentration of PCR products, which includes: (a) immobilizing first primers of PCR primer sets on surfaces of electrodes disposed in a PCR chamber; (b) adding second primers labeled with nanoparticles of the PCR primer sets to the PCR chamber; (c) performing PCR; and (d) measuring the concentration of the PCR products produced on the surfaces of the electrodes by the PCR using an electrochemical method.

In step (d), the electrochemical method may be a voltammetric method, a potentiometric method, an amperometric method, or an impedimetric method.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described more specifically by Examples. However, the following Examples are provided only for illustrations and thus the present invention is not limited to or by them.

EXAMPLES

Example 1

Immobilization of Oligonucleotides on Surfaces of Sold Electrodes

In this Example, thiol-modified oligonucleotides were immobilized on surfaces of gold electrodes in the following manner.

First, gold electrodes were dipped in a mixed solution of sulfuric acid and hydrogen peroxide ($H_2O_2$) (3:1, by volume) and incubated at 60-70° C. for 15 minutes. Then, the gold electrodes were twice or three times washed with distilled water and dried under a nitrogen gas.

Next, thiol-modified oligonucleotides were allowed to react with the surfaces of the gold electrodes for 2 hours. Then, the gold electrodes were washed with a buffer to remove unreacted oligonucleotides.

Next, a 0.1 mM aqueous solution of mercaptohexanol was allowed to react with the gold electrodes for 30 minutes and washed with a buffer to remove unreacted mercaptohexanol, followed by drying.

Example 2

Preparation of Gold Nanoparticles-Labeled Oligonucleotides

First, a 300 nM solution of (alkanthiol)oligonucleotides was added to 0.87 mL of colloidal gold and incubated at room temperature for 16 hours.

Next, the resultant solution was added to a 10 mM phosphate buffered solution (pH 7.0, 0.1M NaCl) and incubated at room temperature for 40 hours. A solution was then removed by centrifugation at 14,000 rpm for 25 hours to give a red oil.

Next, a 10 mM phosphate buffered solution (0.1M NaCl) was added to the red oil and centrifuged to remove a solution. The resultant red oil was used after being eluted to an appropriate concentration.

Example 3

PCR and Detection of Electrical Signal Produced by the PCR

Figure 1:
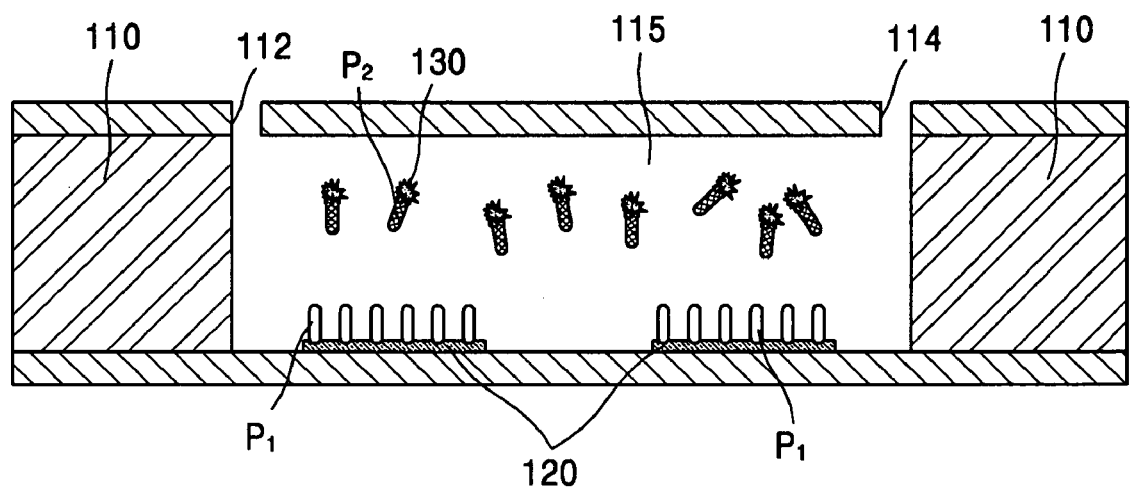
FIG. 1 is a schematic view that illustrates a micro PCR device according to an embodiment of the present invention.

A PCR device for performing PCR using the products of Examples 1 and 2 is illustrated in FIG. 1. Referring to FIG. 1, a plurality of gold electrodes 120 are disposed in a PCR chamber 115 surrounded by a glass wafer 110. First primers $P_1$ among PCR primer sets are immobilized on the surfaces of the gold electrodes 120. The first primers $P_1$ are the thiol-modified oligonucleotides of Example 1. A PCR mixture including second primers $P_2$ is added to the PCR chamber 115. The second primers $P_2$ are the gold nanoparticles-labeled oligonucleotides of Example 2. In FIG. 1, reference numerals 112 and 114 indicate an inlet and an outlet of the PCR chamber 115, respectively.

Figure 2A:
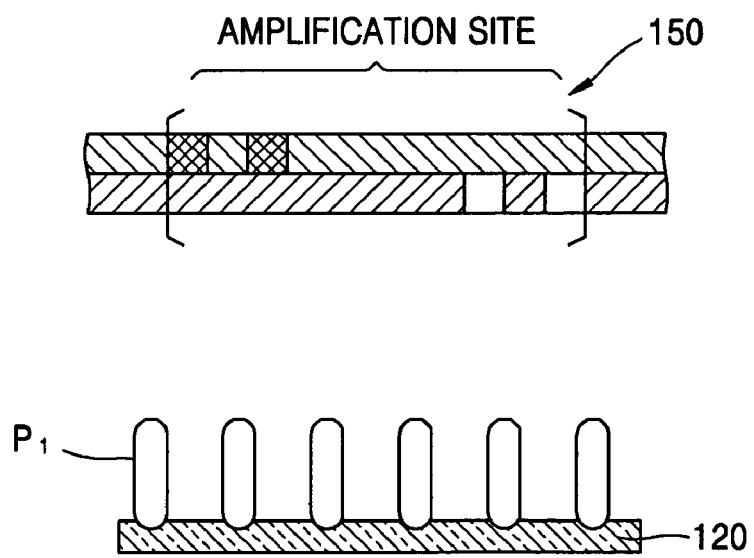
FIGS. 2A through 2G illustrate a process for amplifying nucleic acids according to an embodiment of the present invention.
Figure 2B:
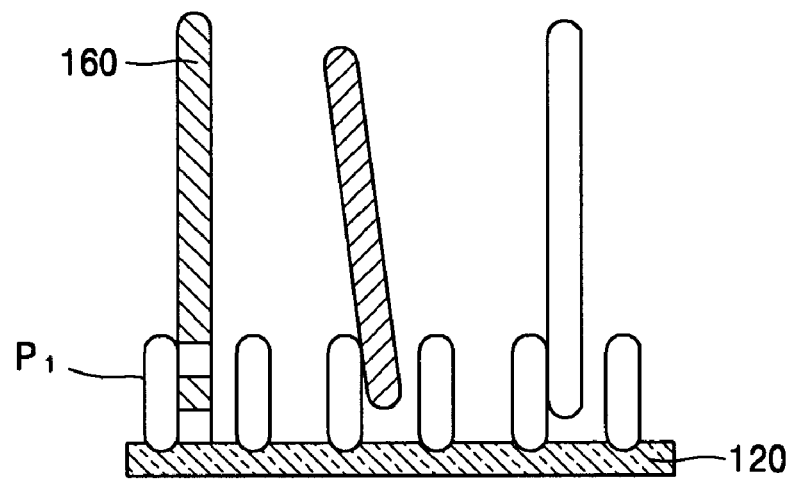
Figure 2C:
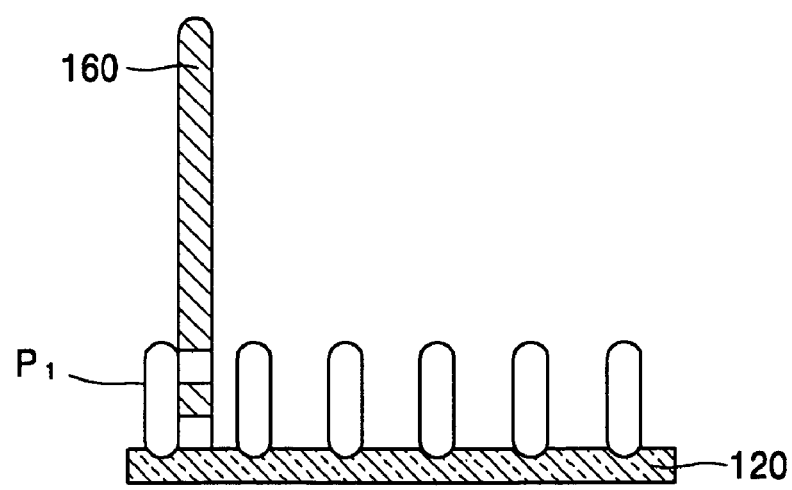
Figure 2D:
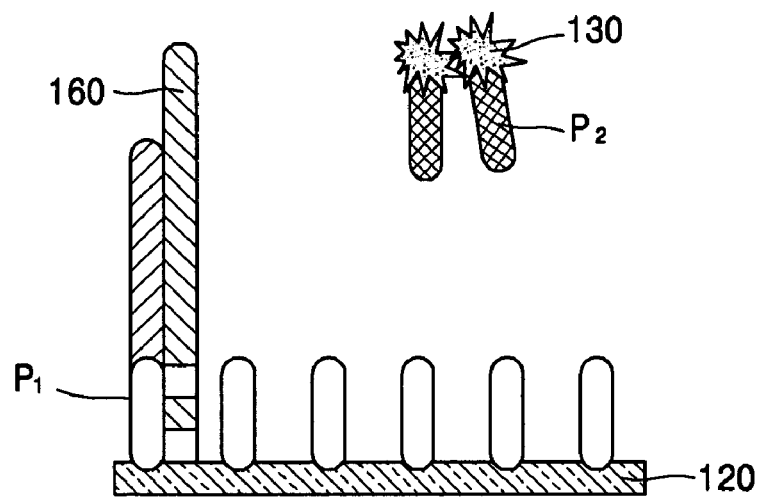
Figure 2E:
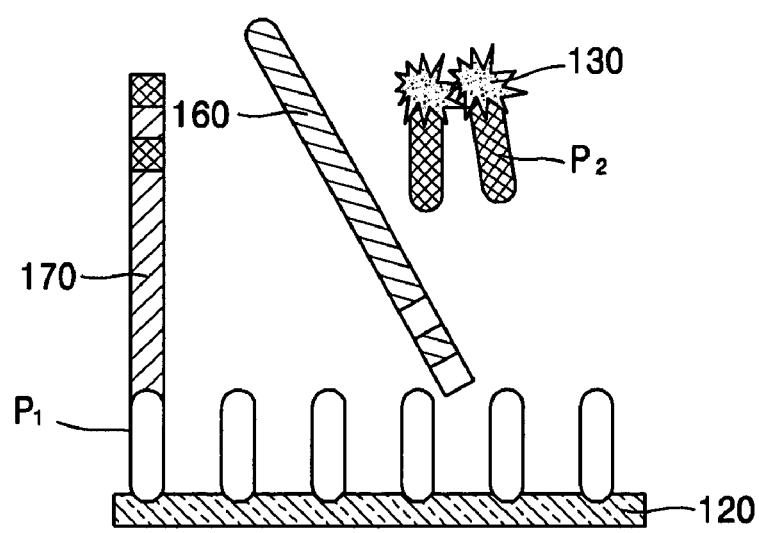
Figure 2F:
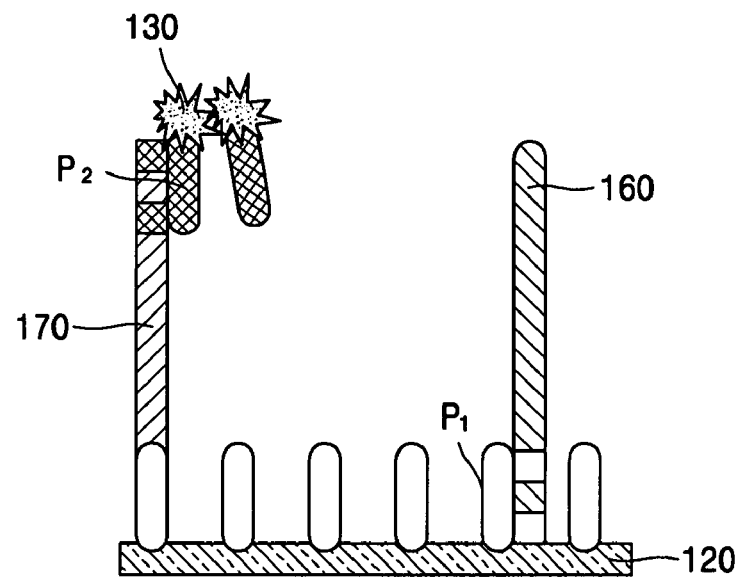
Figure 2G:
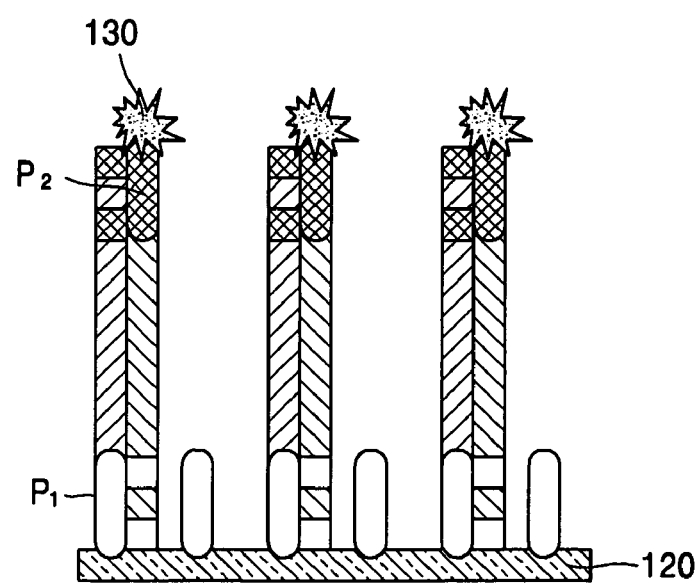

Hereinafter, processes for amplifying nucleic acids using the above-described micro PCR device will be described with reference to FIGS. 2A through 2G. First, double-stranded template HBV DNAs 150 are added to the PCR chamber (FIG. 2A). The double-stranded DNAs 150 are denatured to single strands by adjusting the temperature of the PCR chamber. DNA single strands 160 are bonded complementarily to the first primers P1 immobilized on the surfaces of the gold electrodes 120 (FIG. 2B). Then, the surfaces of the gold electrodes 120 are washed to remove impurities (FIG. 2C). DNA polymerase initiates extension of the first primers P1 to synthesize double-stranded DNAs (FIG. 2D). The DNA single strands 160 used as a template are separated from amplified DNA strands 170 by denaturation (FIG. 2E). The second primers P2 labeled with the gold nanoparticles 130 are bonded complementarily to the amplified DNA strands 170 by annealing (FIG. 2F). Amplification of nucleic acids is completed by repeated cycles of the extension, the denaturation, and the annealing (FIG. 2G).

In this Example, a change in signal emitted from PCR products was measured by impedance measurement method to obtain the concentration of the PCR products in real-time.

Figure 3A:
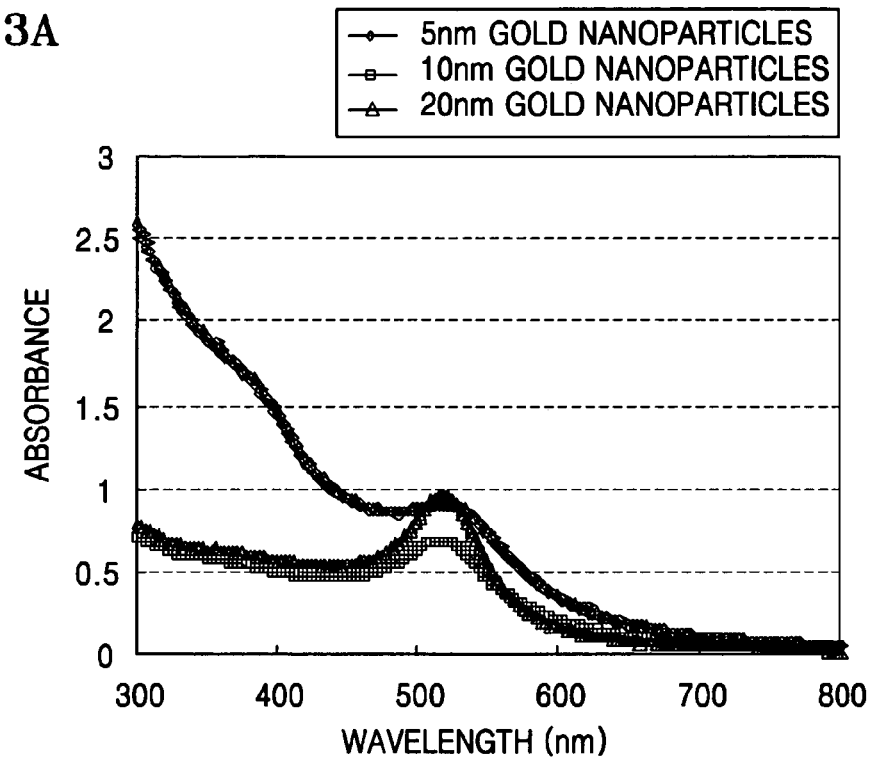
FIGS. 3A and 3B are respectively a UV-vis spectrum of gold nanoparticles and a UV-vis spectrum of gold nanoparticles bonded to thiol-modified oligonucleotides.
Figure 3B:
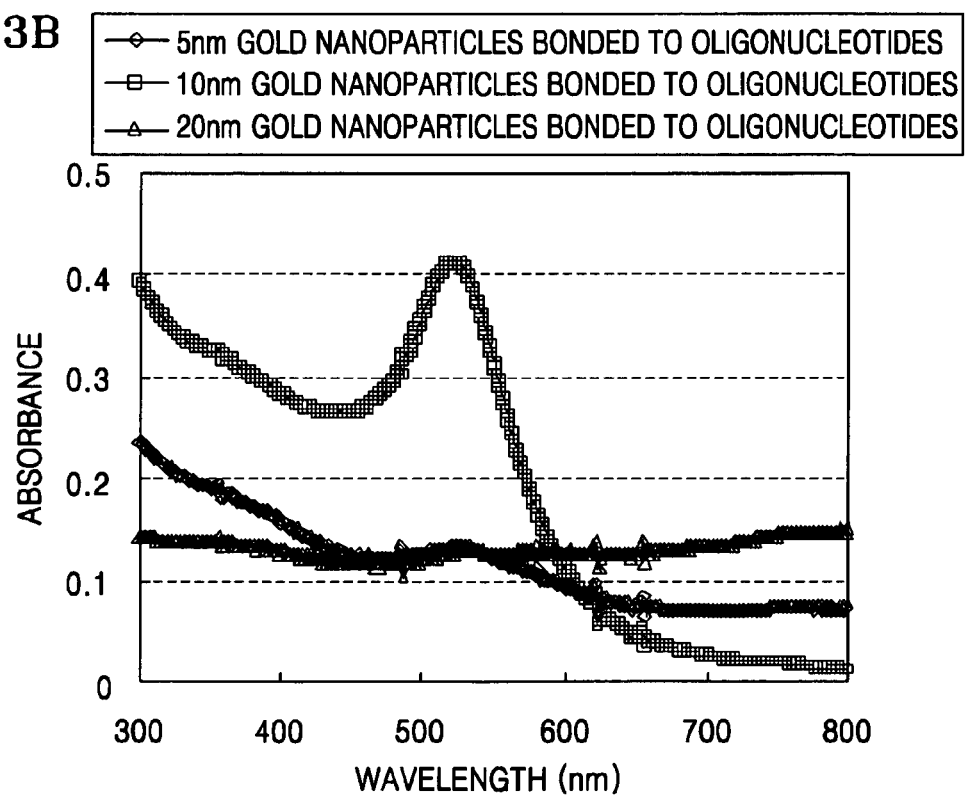

FIGS. 3A and 3B are respectively a UV-vis spectrum of gold nanoparticles and a UV-vis spectrum of gold nanoparticles bonded to thiol-modified oligonucleotides. In detail, FIG. 3A illustrates a UV-vis spectrum of gold nanoparticles of three different sizes (5 nm, 10 nm, and 20 nm) and FIG. 3B illustrates a UV-vis spectrum of gold nanoparticles of three different sizes (5 nm, 10 nm, and 20 nm) bonded to thiol-modified oligonucleotides. As shown in FIG. 3A, the three types gold nanoparticles exhibited an absorption band at 518 nm. However, as shown in FIG. 3B, in reaction between the gold nanoparticles and the thiol-modified oligonucleotides, while 5 nm and 20 nm gold nanoparticles did not react with the thiol-modified oligonucleotides due to precipitation, 10 nm gold nanoparticles were labeled to the thiol-modified oligonucleotides.

Figure 4:
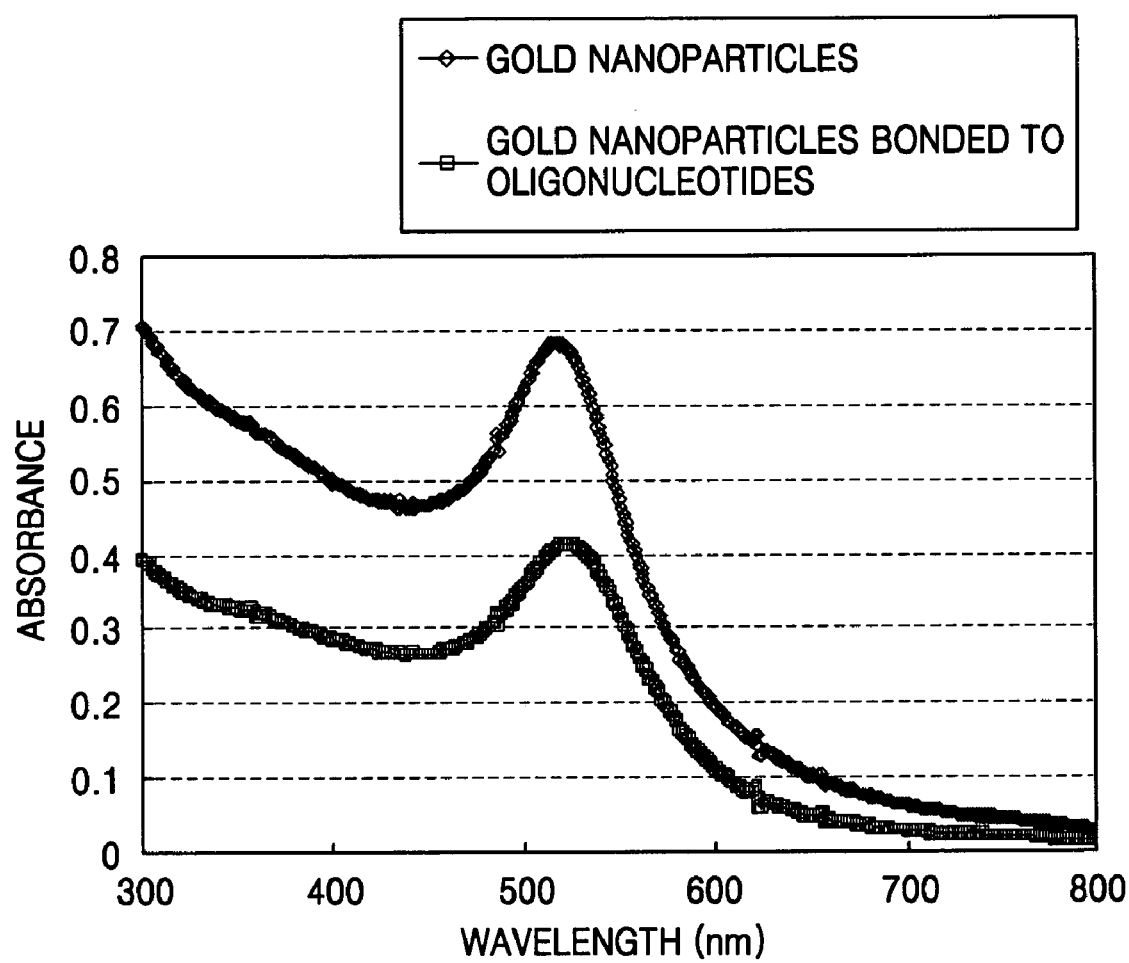
FIG. 4 is a UV-vis spectrum of 10 nm gold nanoparticles before and after being bonded to thiol-modified oligonucleotides.

FIG. 4 is a UV-vis spectrum of 10 nm gold nanoparticles before and after being bonded to thiol-modified oligonucleotides. Referring to FIG. 4, it can be seen that the absorption band of the 10 nm gold nanoparticles was shifted from 518 nm to 523 nm after being bonded to the thiol-modified oligonucleotides.

Figure 5:
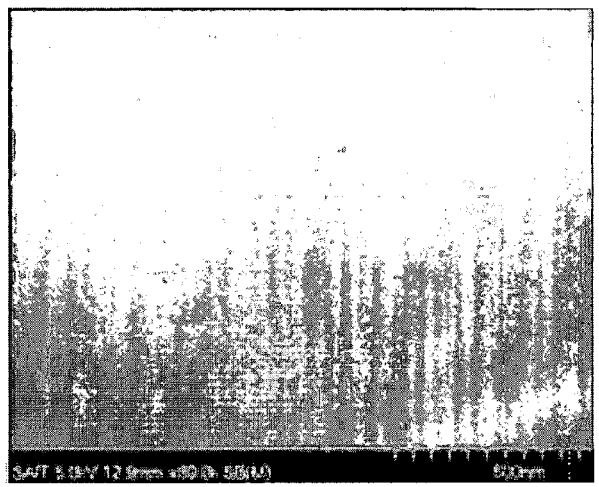
FIG. 5 illustrates field emission scanning electron microscopic (FE-SEM) images of surfaces of gold electrodes, (a) as untreated, (b) after immobilization of probe oligonucleotides, and (c) after hybridization using target oligonucleotides labeled with nanoparticles.
Figure 5:
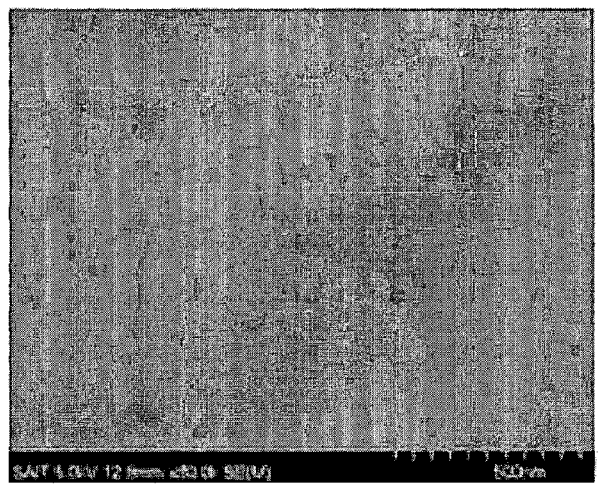
Figure 5:
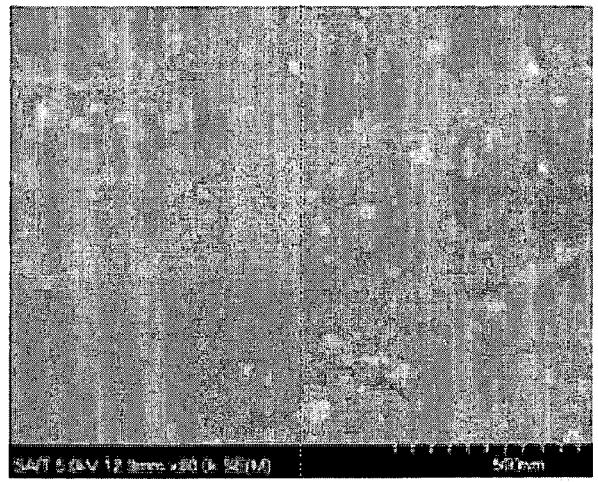

FIG. 5 illustrates field emission scanning electron microscopic (FE-SEM) images of surfaces of gold electrodes, (a) as untreated, (b) after immobilization of probe oligonucleotides, and (c) after hybridization using target oligonucleotides labeled with gold nanoparticles.

Figure 6A:
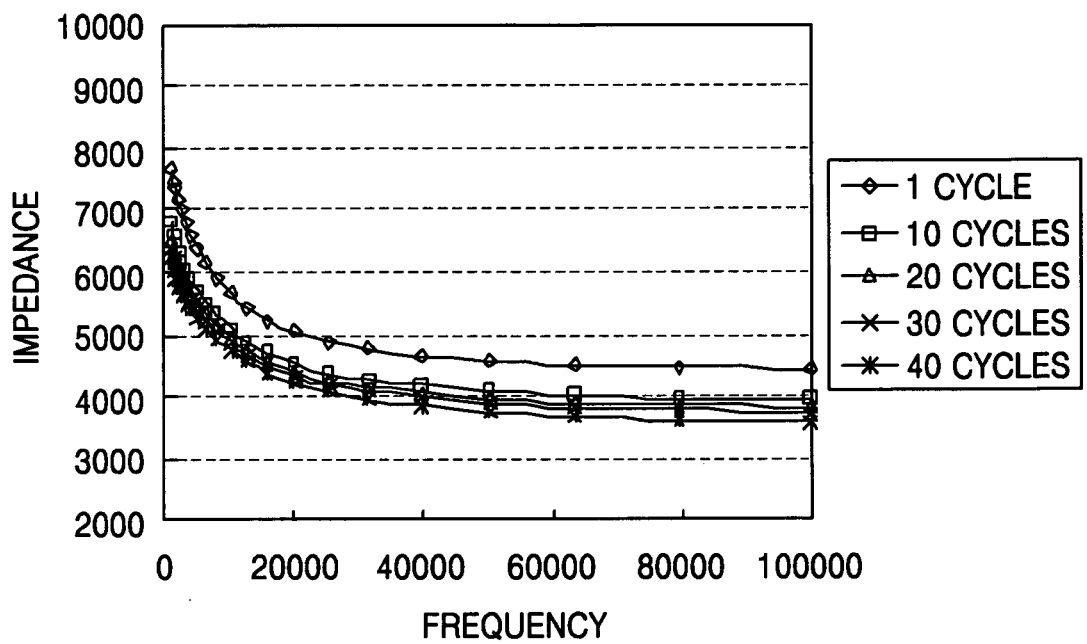
FIGS. 6A and 6B are impedance Bode plots for PCR products with using $10^6$ copies of HBV DNAs as a template and without using a template, respectively.
Figure 6B:
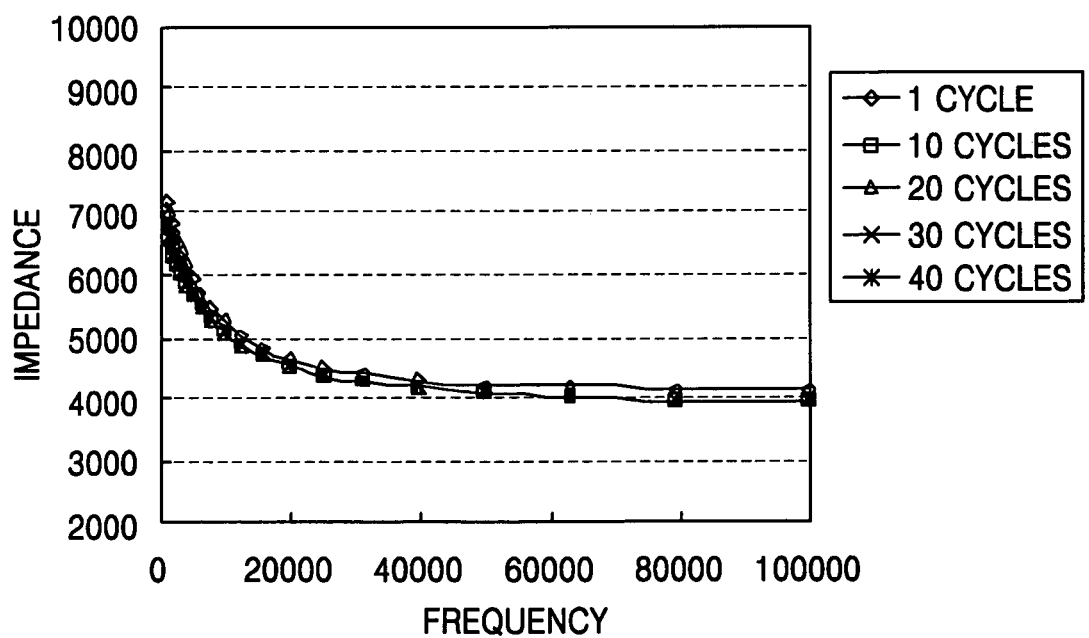
Figure 7A:
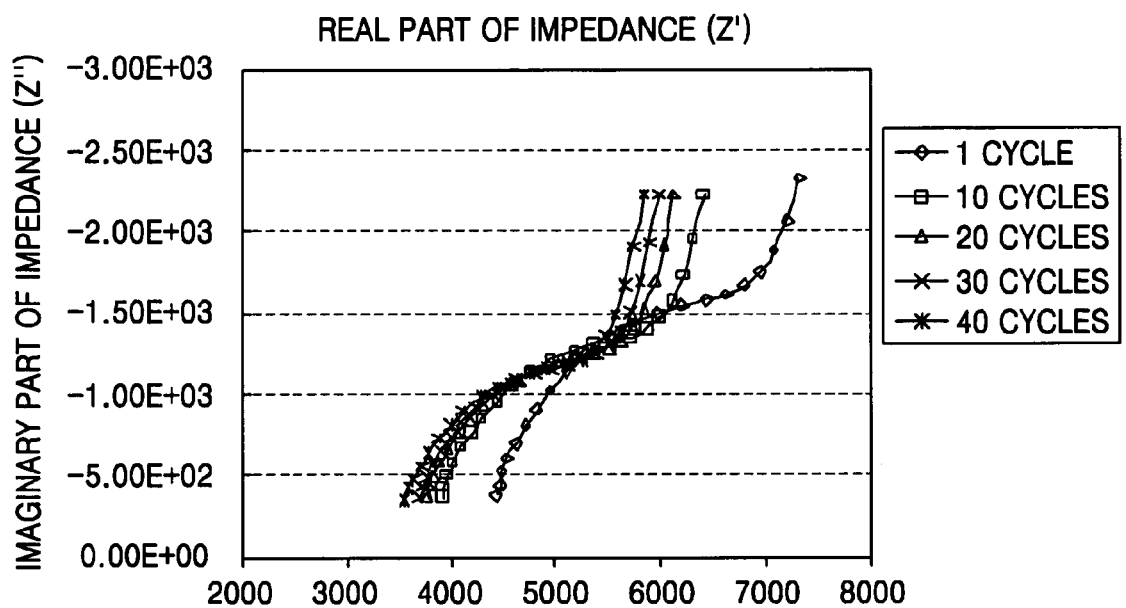
FIGS. 7A and 7B are Nyquist plots of the results of FIGS. 6A and 6B.
Figure 7B:
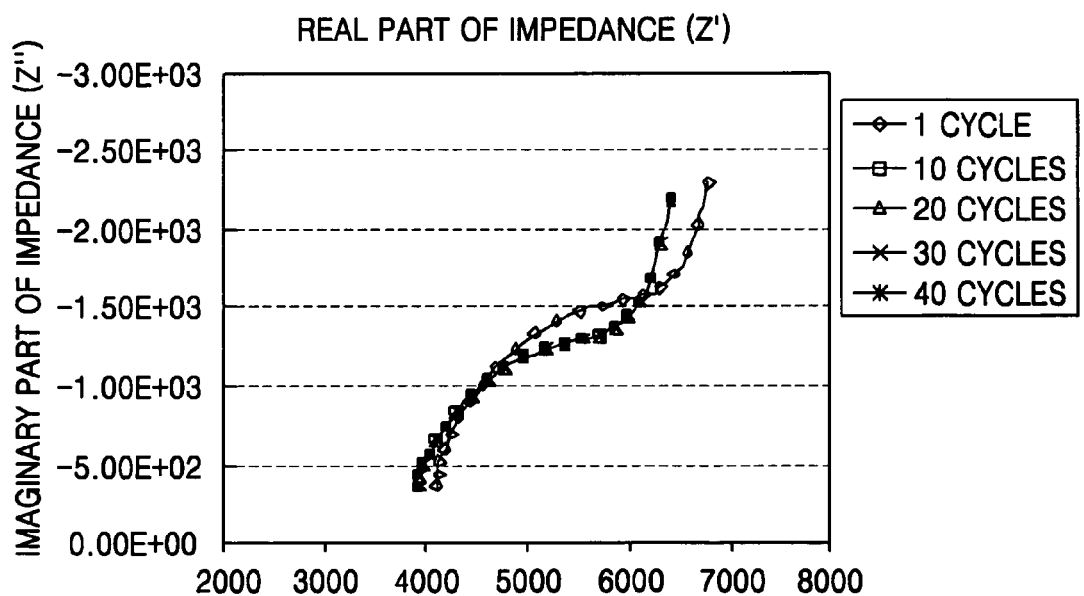
Figure 8A:
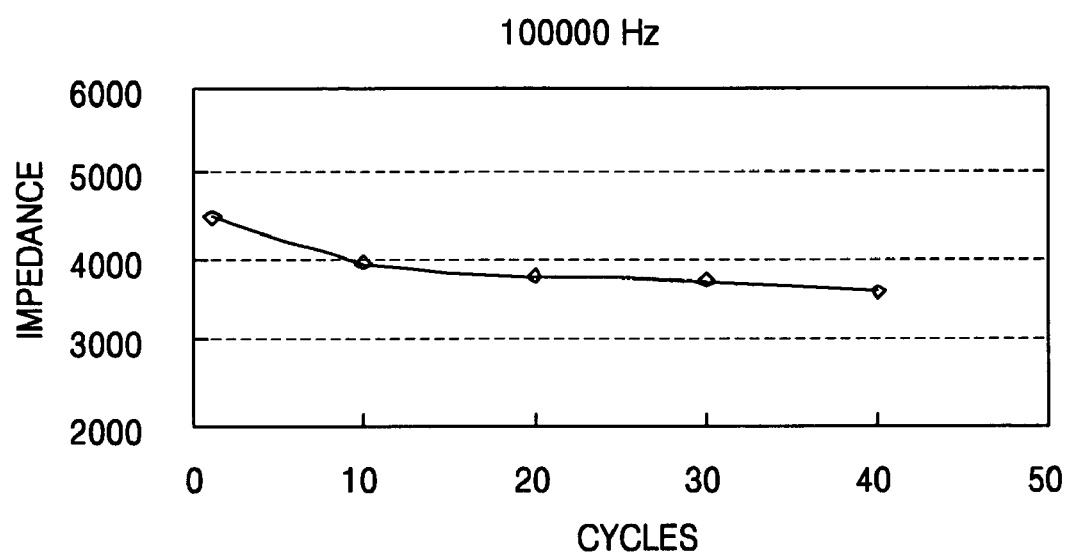
FIGS. 8A and 8B are graphs of impedances of PCR products versus PCR cycles under experimental conditions of 100,000 Hz sweep, an alternating current (AC) voltage of 10 mV, and 40 PCR cycles, with using $10^6$ copies of HBV DNAs as a template and without using a template, respectively.
Figure 8B:
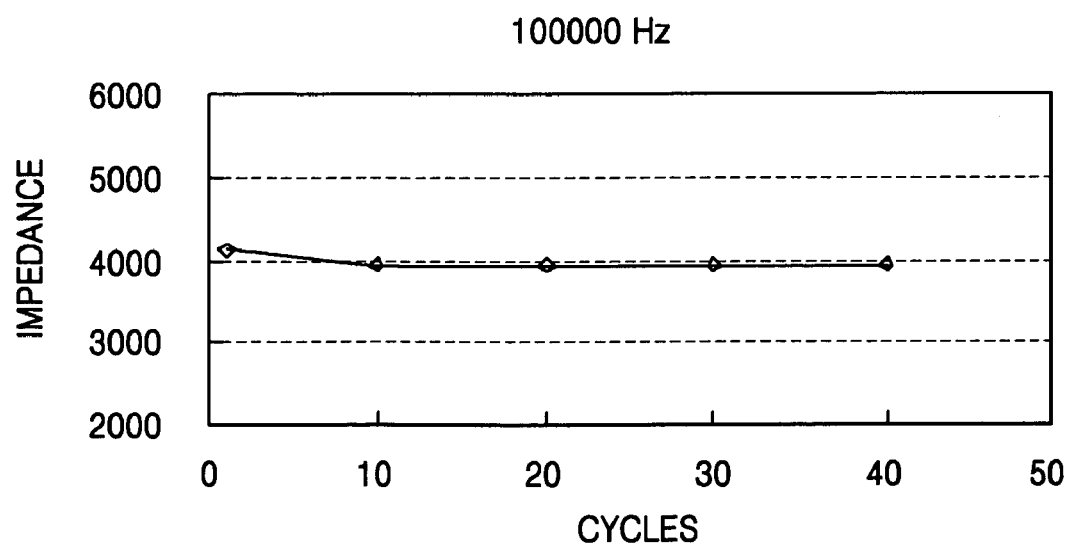
Figure 9A:
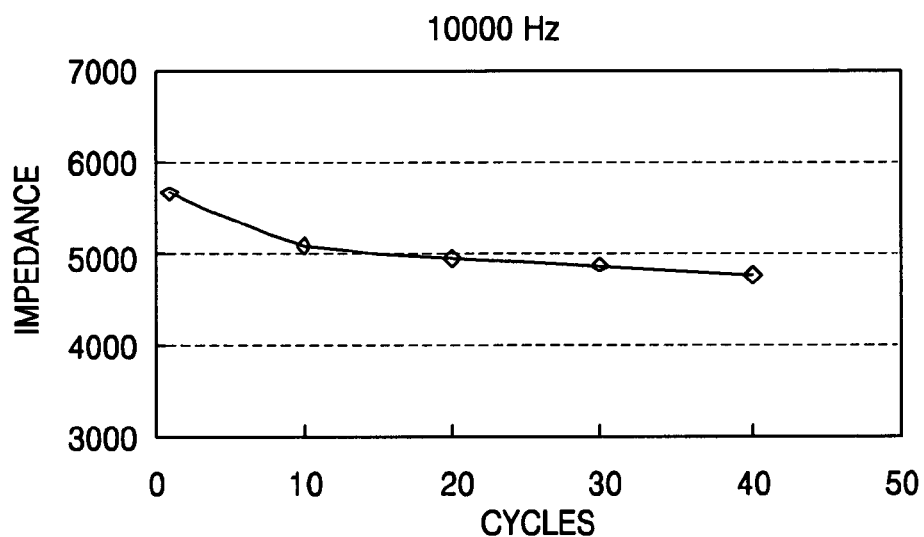
FIGS. 9A and 9B are graphs of impedances of PCR products versus PCR cycles under experimental conditions of 10,000 Hz sweep, an AC voltage of 10 mV, and 40 PCR cycles, with using $10^6$ copies of HBV DNAs as a template and without using a template, respectively.
Figure 9B:
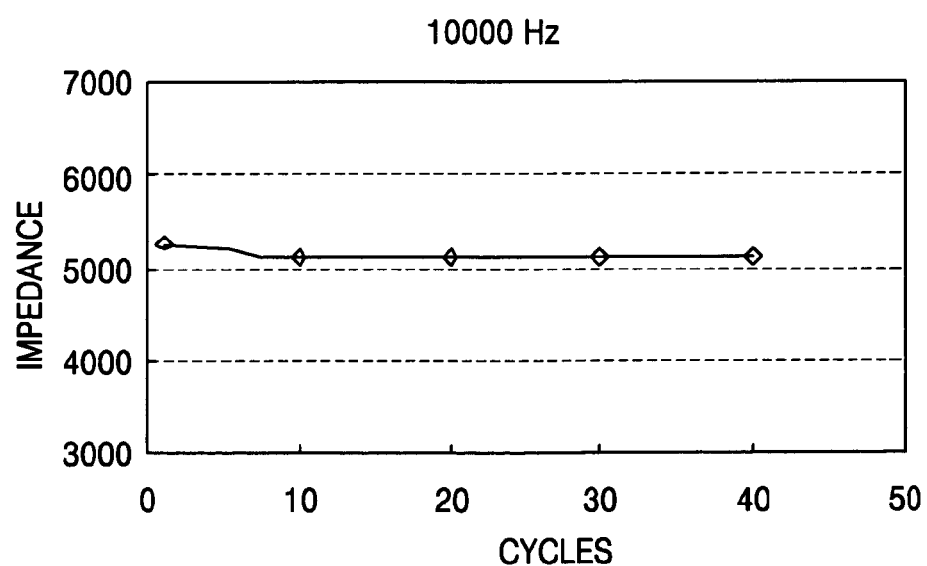
Figure 10A:
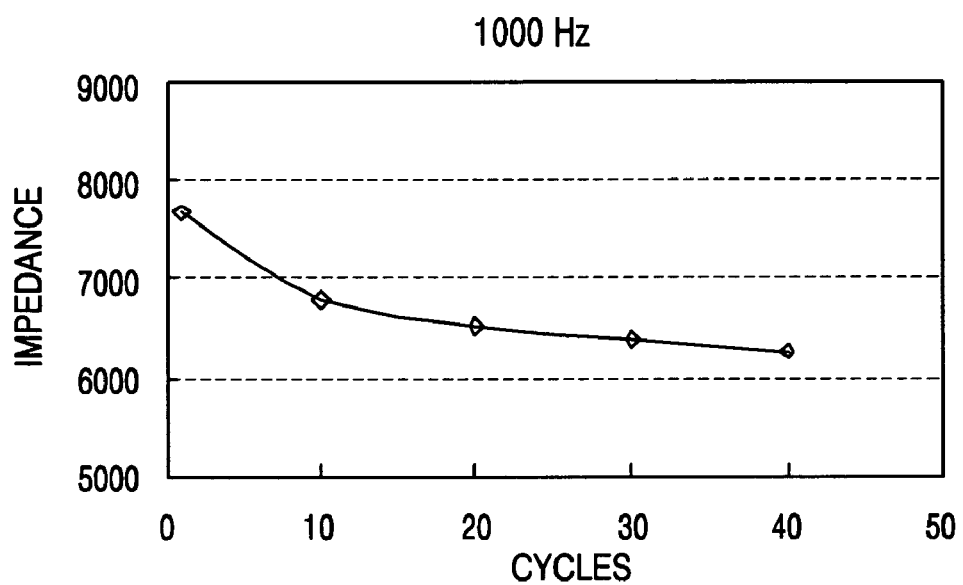
FIGS. 10A and 10B are graphs of impedances of PCR products versus PCR cycles under experimental conditions of 1,000 Hz sweep, an AC voltage of 10 mV, and 40 PCR cycles, with using $10^6$ copies of HBV DNAs as a template and without using a template, respectively.
Figure 10B:
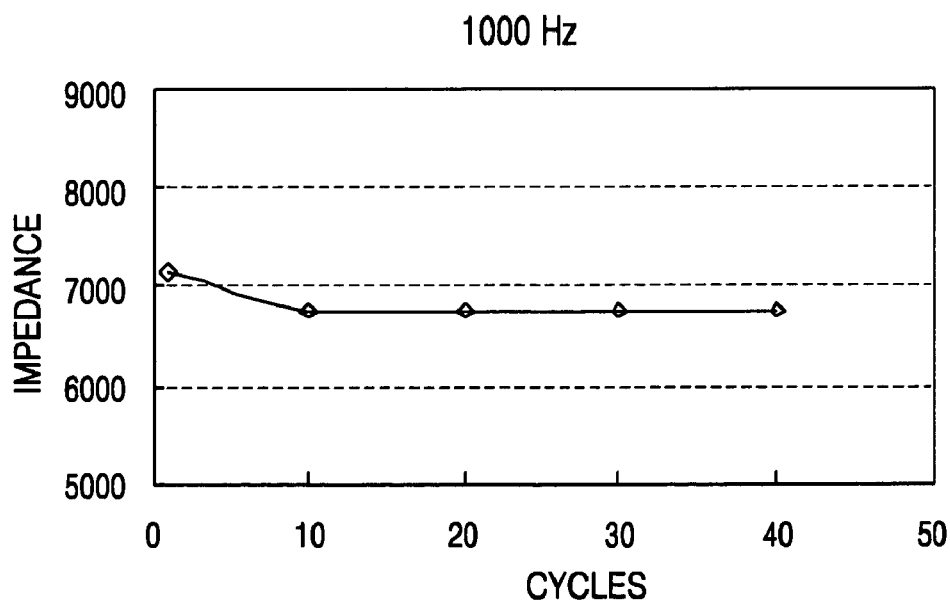

FIGS. 6A and 6B are impedance Bode plots for PCR products with using $10^6$ copies of HBV DNAs as a template and without using a template, respectively. Here, experimental conditions were as follows: 1,000-100,000 Hz sweep, alternating current (AC) voltage of 10 mV, and 40 cycles of PCR. FIGS. 7A and 7B are Nyquist plots of the results of FIGS. 6A and 6B.

Referring to FIGS. 6A through 7B, with respect to using $10^6$ copies of HBV DNAs as a template, impedances varied according to the cycles of PCR. On the other hand, with respect to using no templates, no change in impedances versus the cycles of PCR was observed.

FIGS. 8A and 8B, 9A and 9B, and 10A and 10B are graphs of impedances of PCR products versus PCR cycles with using $10^6$ copies of HBV DNAs as a template and without using a template. Experimental conditions for FIGS. 8A and 8B were set to 100,000 Hz, an AC voltage of 10 mV, and 40 PCR cycles, experimental conditions for FIGS. 9A and 9B were set to 10,000 Hz, an AC voltage of 10 mV, and 40 PCR cycles, and experimental conditions for FIGS. 10A and 10B were set to 1,000 Hz, AC voltage of 10 mV, and 40 PCR cycles.

Referring to FIGS. 8A through 10B, with respect to using $10^6$ copies of HBV DNAs as a template, impedances were reduced as the number of PCR cycles increased. On the other hand, with respect to using no templates, little change in impedances versus PCR cycles were observed.

According to the experiments as described above, when PCR is performed on the surfaces of electrodes disposed in a PCR chamber by immobilizing first primers on the surfaces of the electrodes and adding second primers labeled with nanoparticles to a PCR mixture, PCR products can be detected in real-time. Therefore, high detection sensitivity and reproducibility can be ensured.

As apparent from the above description, according to the present invention, PCR is performed on the surfaces of electrodes using primers labeled with nanoparticles. Therefore, PCR products can be detected in real-time with high sensitivity and reproducibility without transferring the PCR products to a separate detection system. Furthermore, since signals emitted from the nanoparticles can be detected by various electrochemical methods, detection results can be assayed with high accuracy.

While the present invention has been particularly shown and described with reference to exemplary embodiments thereof, it will be understood by those of ordinary skill in the art that various changes in form and details may be made therein without departing from the spirit and scope of the present invention as defined by the following claims.

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: probe polynucleotide which is immobilized on
      the electrod surface
<220> FEATURE:
<221> NAME/KEY: misc_feature
<222> LOCATION: (1)

-continued

```
<223> OTHER INFORMATION: HS-(CH2)6- attached at 5' OH site : -SH group
      is used for the immobilized of the probe to the electrode

<400> SEQUENCE: 1
agcagaggcg gtgtcgagga gat                                           23

<210> SEQ ID NO 2
<211> LENGTH: 33
<212> TYPE: DNA
<213> ORGANISM: Artificial Sequence
<220> FEATURE:
<223> OTHER INFORMATION: 2nd primer
<220> FEATURE:
<221> NAME/KEY: misc_feature
<222> LOCATION: (1)
<223> OTHER INFORMATION: HS-(CH2)15- attached at the 5 OH site : -SH
      group is used for the nanoparticle attachment

<400> SEQUENCE: 2 ttttttttt gctttggggc atggacattg acc                                 33
```

What is claimed is:

1. A micro polymerase chain reaction ("PCR") device comprising:
   a PCR chamber having electrodes;
   a set of PCR primers having first primers and second primers, wherein the first primers are immobilized on surfaces of the electrodes and the second primers, which are the only primers labeled with nanoparticles, are disposed in the PCR chamber; and
   a PCR product detection unit detecting in real-time PCR products produced on the surfaces of the electrodes using an electrochemical detection method,
   wherein the first primer bonds to a single strand of a target molecule, the first primer then extends to synthesize a complementary strand of the target molecule, the single strand of the target molecule is removed from the extended first primer, and then the second primer bonds to the extended first primer and extends to synthesize a strand which is complementary to the extended first primer.

2. The micro PCR device of claim 1, wherein the electrochemical detection method is a voltammetric detection method, a potentiometric detection method, an amperometric detection method, or an impedimetric detection method.

3. The micro PCR device of claim 1, wherein the second primers are thiol-modified oligonucleotides labeled with gold nanoparticles.

4. The micro PCR device of claim 3, wherein the gold nanoparticles have a particle size of about 10 nm.

5. The micro PCR device of claim 1, wherein the electrodes are made of gold.

6. The micro PCR device of claim 5, wherein the first primers are thiol-modified oligonucleotides.

7. A method for measuring the concentration of polymerase chain reaction ("PCR") products, the method comprising:
   immobilizing a first primer of a PCR primer set on surfaces of electrodes disposed in a PCR chamber;
   adding a second primer of the PCR primer set to the PCR chamber;
   bonding the first primers to a single strand of a target molecule;
   extending the first primer to synthesize a complementary strand of the target molecule;
   removing the single strand of the target molecule from the extended first primer;
   bonding the second primer, which is the only primer labeled with a nanoparticle, to the extended first primer;
   extending the second primer to synthesize a strand which is complementary to the extended first primer; and
   measuring the concentration of the PCR products produced by the PCR on the surfaces of the electrodes, wherein the measuring the concentration uses an electrochemical method.

8. The method of claim 7, wherein the electrochemical method is a voltammetric method, a potentiometric method, an amperometric method, or an impedimetric method.

9. The method of claim 7, wherein the second primers are thiol-modified oligonucleotides labeled with gold nanoparticles.

* * * * *